(12) United States Patent
Faust

(10) Patent No.: US 9,151,699 B2
(45) Date of Patent: Oct. 6, 2015

(54) APPARATUS AND METHOD FOR TAKING SAMPLES

(75) Inventor: Horst Faust, Dorsten (DE)

(73) Assignee: FL-SMIDTH A/S (DK)

( * ) Notice: Subject to any disclaimer, the term of this patent is extended or adjusted under 35 U.S.C. 154(b) by 373 days.

(21) Appl. No.: 13/880,166

(22) PCT Filed: Oct. 18, 2011

(86) PCT No.: PCT/EP2011/068159
§ 371 (c)(1),
(2), (4) Date: Apr. 18, 2013

(87) PCT Pub. No.: WO2012/052421
PCT Pub. Date: Apr. 26, 2012

(65) Prior Publication Data
US 2013/0220036 A1    Aug. 29, 2013

(30) Foreign Application Priority Data
Oct. 19, 2010   (DE) .......................... 10 2010 038 279

(51) Int. Cl.
*G01N 1/20* (2006.01)
*G01N 1/22* (2006.01)
*G01N 1/02* (2006.01)

(52) U.S. Cl.
CPC .. *G01N 1/02* (2013.01); *G01N 1/20* (2013.01); *G01N 1/22* (2013.01); *G01N 1/2247* (2013.01); *G01N 2001/2092* (2013.01)

(58) Field of Classification Search
CPC ............................................. G01N 2001/2092
USPC ................. 73/863.41, 863.43, 863.51, 863.56
See application file for complete search history.

(56) References Cited

U.S. PATENT DOCUMENTS

| 887,615 A | * | 5/1908 | Fenstermaker ............ 73/863.41 |
| 2,020,529 A | * | 11/1935 | Thorsten .................... 73/863.23 |

(Continued)

FOREIGN PATENT DOCUMENTS

| DE | 2837369 A1 | 3/1980 |
| DE | 160734 A3 | 2/1984 |

(Continued)

OTHER PUBLICATIONS

International Search Report and Written Opinion dated Nov. 28, 2011, 17 pages.

*Primary Examiner* — Laura Martin
*Assistant Examiner* — Herbert K Roberts
(74) *Attorney, Agent, or Firm* — Aaron M. Pile; Daniel DeJoseph; Matthew R. Weaver

(57) ABSTRACT

The invention relates to a device (1) for sampling, comprising a housing (2) having a housing chamber (8) which has two connection openings (10) for connecting one line portion in each case. The device (1) includes a withdrawal element (13) which is movable in the housing chamber (8). The withdrawal element is formed, at least in portions, in a profile-like manner, and bounds a hollow sampling region (19), extending along a profile longitudinal direction course (16), at the periphery of the sampling region, while leaving an entry opening (21) which extends along an opening longitudinal direction course (20). Guide means are provided by means of which a defined movement pattern of the withdrawal element (13) in the housing chamber (8) is predetermined, via which movement pattern at least one of the two opening cross-sections (32) in a projection view perpendicular thereto may be traversed over the entire area by means of the entry opening (21). The invention proposes that as a result of the movement pattern specified by the guide means, an orientation of the withdrawal element (13) in an observation plane which moves with the withdrawal element relative to a geometric intersection line of the observation plane with a nonmoving geometric reference plane which extends perpendicular to the observation plane and to at least one opening cross-section (32), remains the same when the withdrawal element (13) is moved.

15 Claims, 14 Drawing Sheets

(56) References Cited

U.S. PATENT DOCUMENTS

Figure 4:
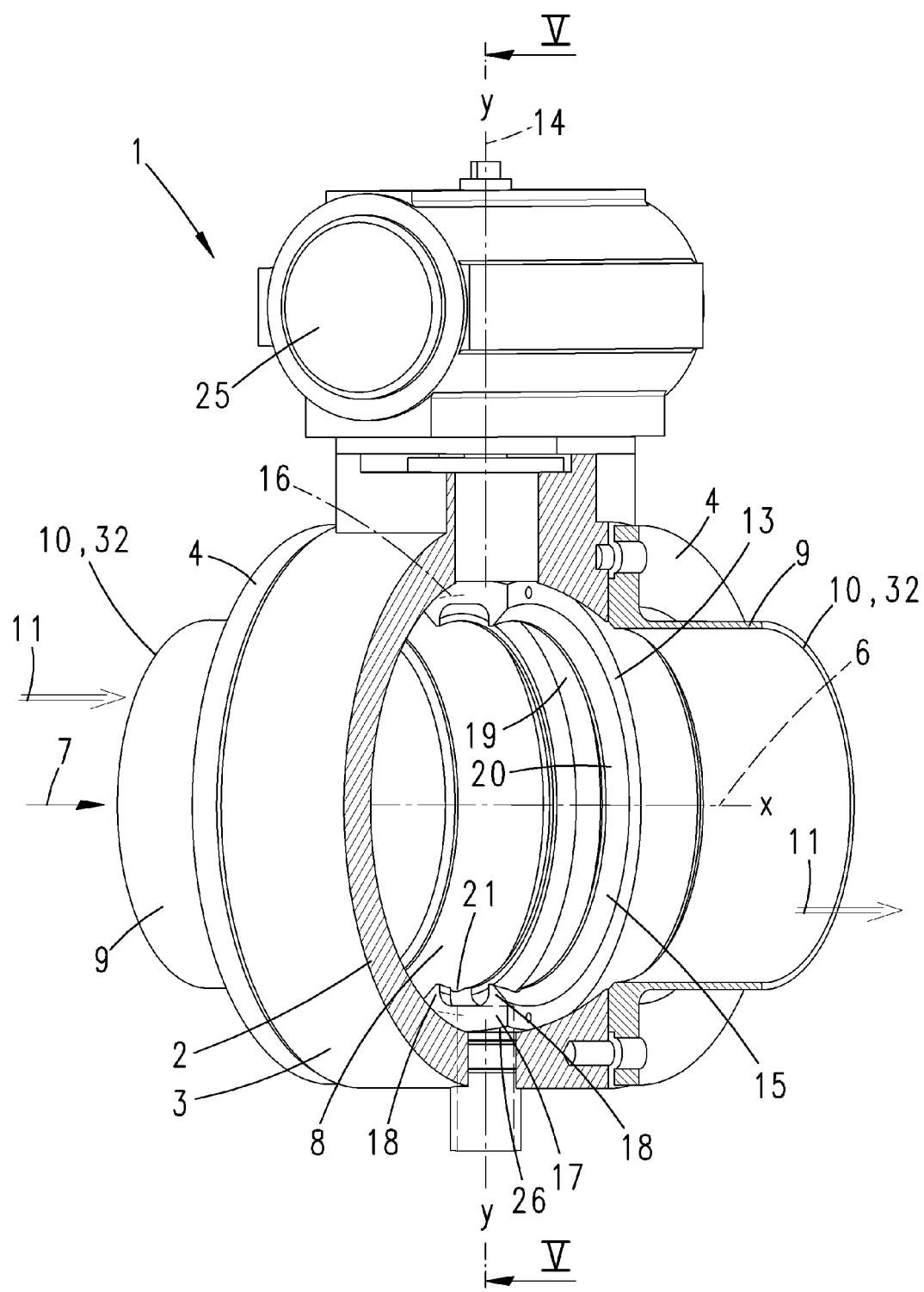

| | | | |
|---|---|---|---|
| 2,641,934 A * | 6/1953 | Werts | 73/863.82 |
| 2,740,291 A * | 4/1956 | Brown | 73/152.23 |
| 3,783,695 A * | 1/1974 | Grothe et al. | 73/863.56 |
| 4,082,004 A | 4/1978 | Weber et al. | |
| 4,112,772 A * | 9/1978 | McDevitt | 73/864.57 |
| 4,207,922 A * | 6/1980 | Andrieux et al. | 137/625.11 |
| 4,346,609 A * | 8/1982 | Diesel | 73/863.33 |
| 4,946,650 A * | 8/1990 | Rothele | 422/68.1 |
| 4,967,797 A * | 11/1990 | Manska | 137/625.47 |
| 4,972,844 A * | 11/1990 | Cianci et al. | 600/573 |
| 5,878,813 A * | 3/1999 | Ridgeway, Jr. | 166/162 |
| 2004/0063478 A1* | 4/2004 | Kormann et al. | 460/1 |
| 2004/0156746 A1* | 8/2004 | Larsen | 422/58 |
| 2007/0275474 A1* | 11/2007 | Hartonen et al. | 436/155 |
| 2009/0205446 A1* | 8/2009 | Lyman | 73/863.91 |

FOREIGN PATENT DOCUMENTS

| | | | |
|---|---|---|---|
| DE | 293177 A5 | 8/1991 | |
| DE | 19721104 A1 | 11/1998 | |
| DE | 19909437 A1 | 9/2000 | |
| DE | 10115029 A1 | 10/2002 | |
| DE | 202005009457 U1 | 11/2005 | |
| DE | 102006049423 A1 | 4/2008 | |
| EP | 332305 A1 * | 9/1989 | G01N 1/00 |
| EP | 373281 A1 * | 6/1990 | G01N 1/20 |

* cited by examiner

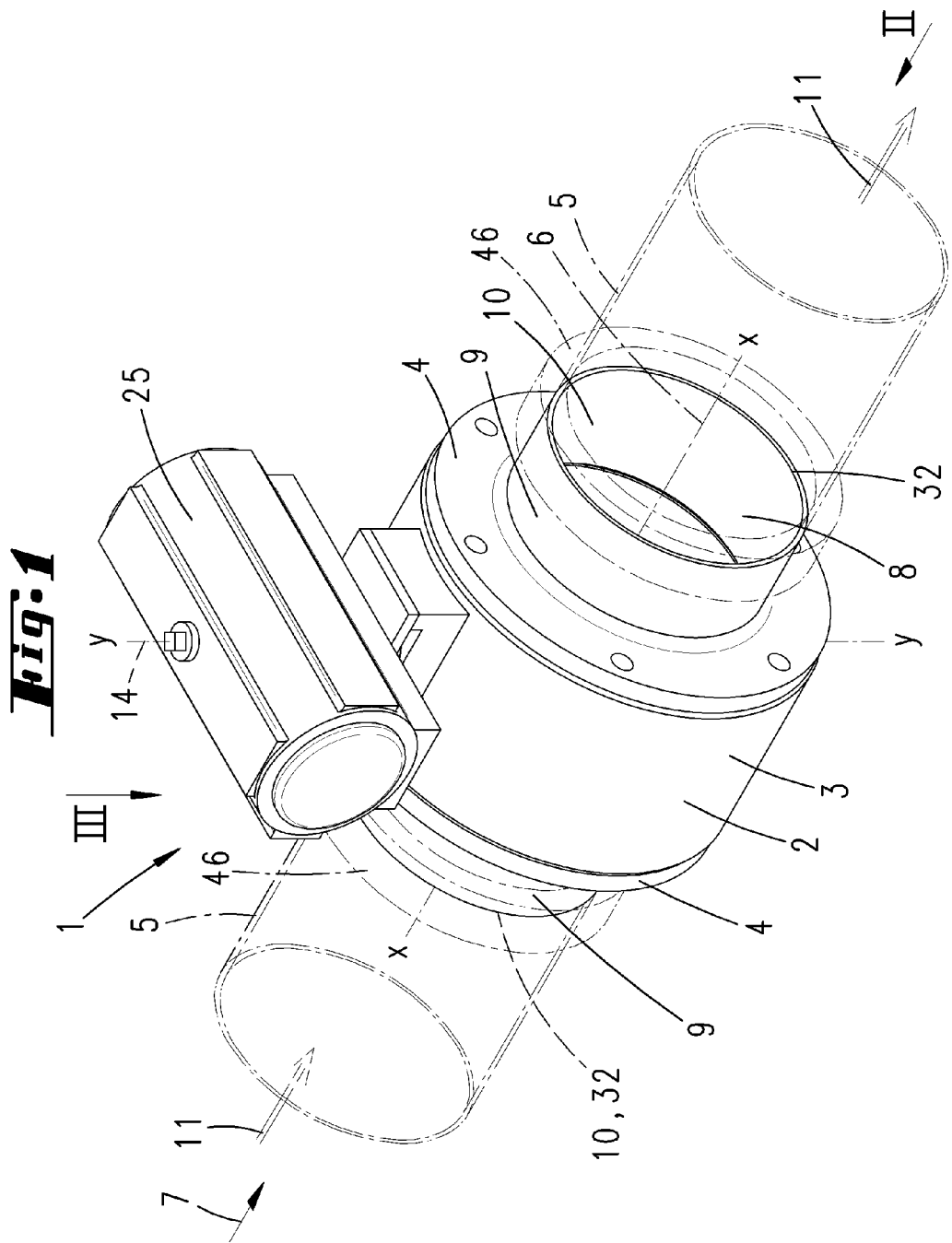

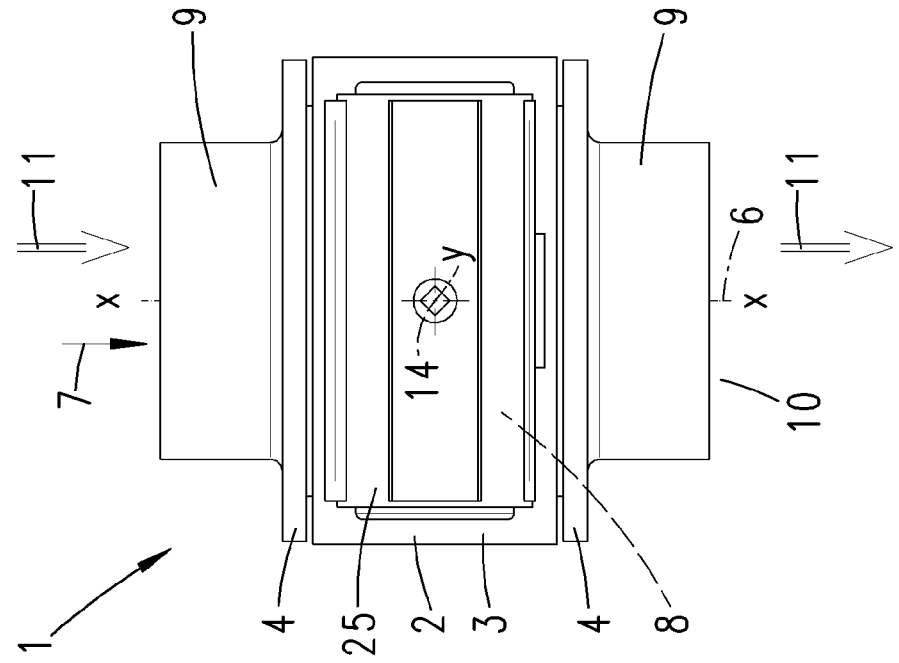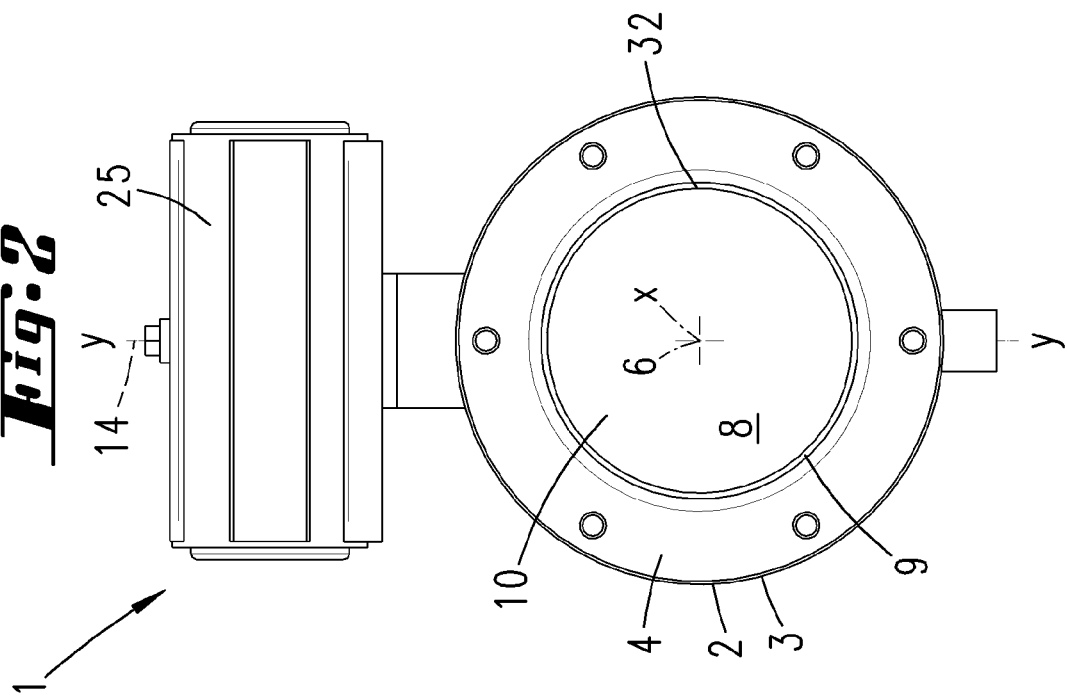

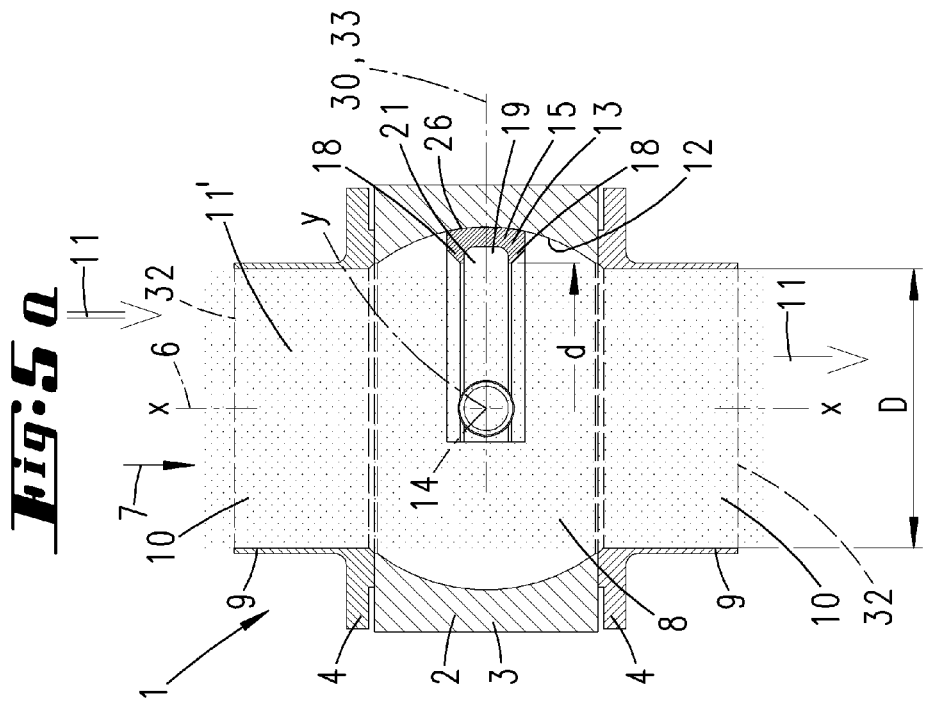
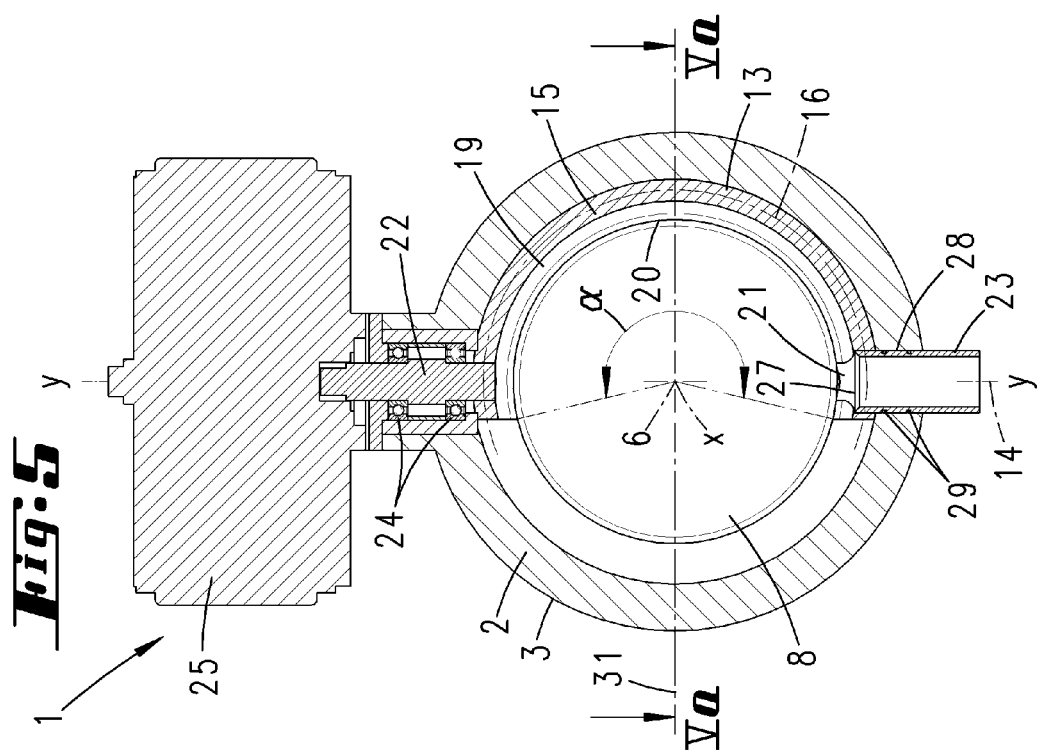

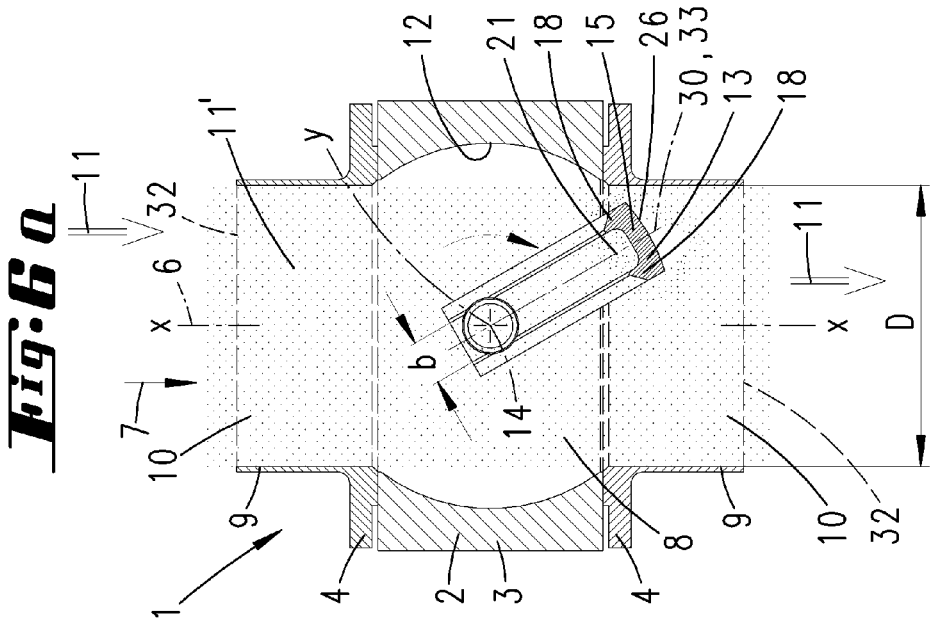
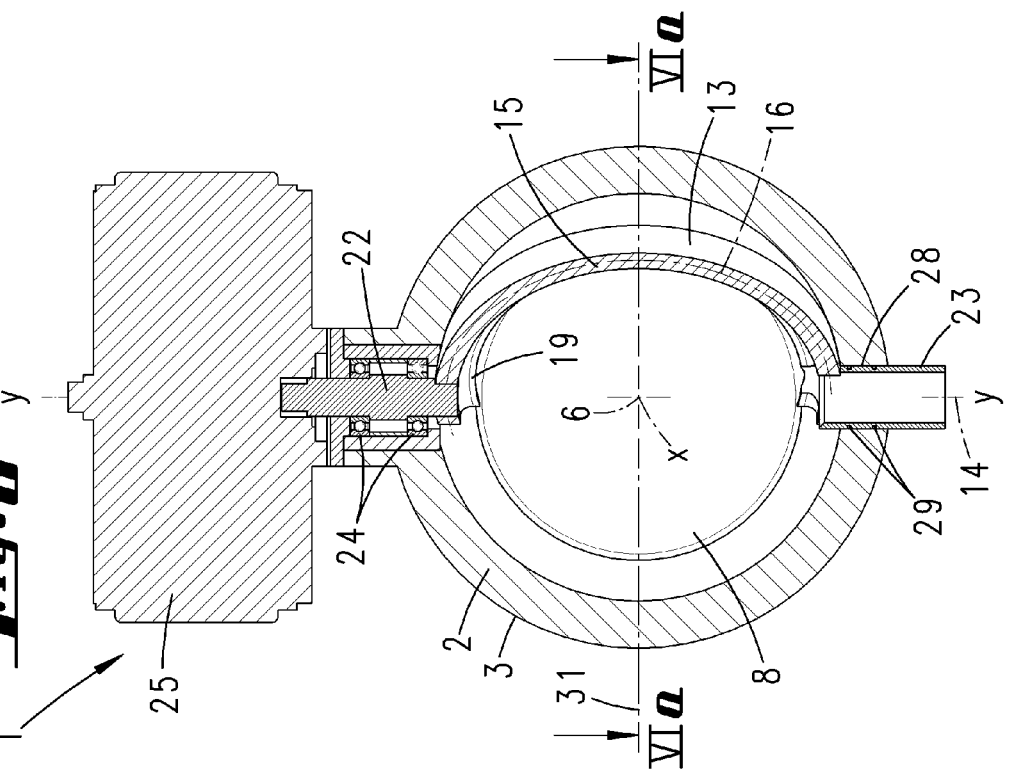

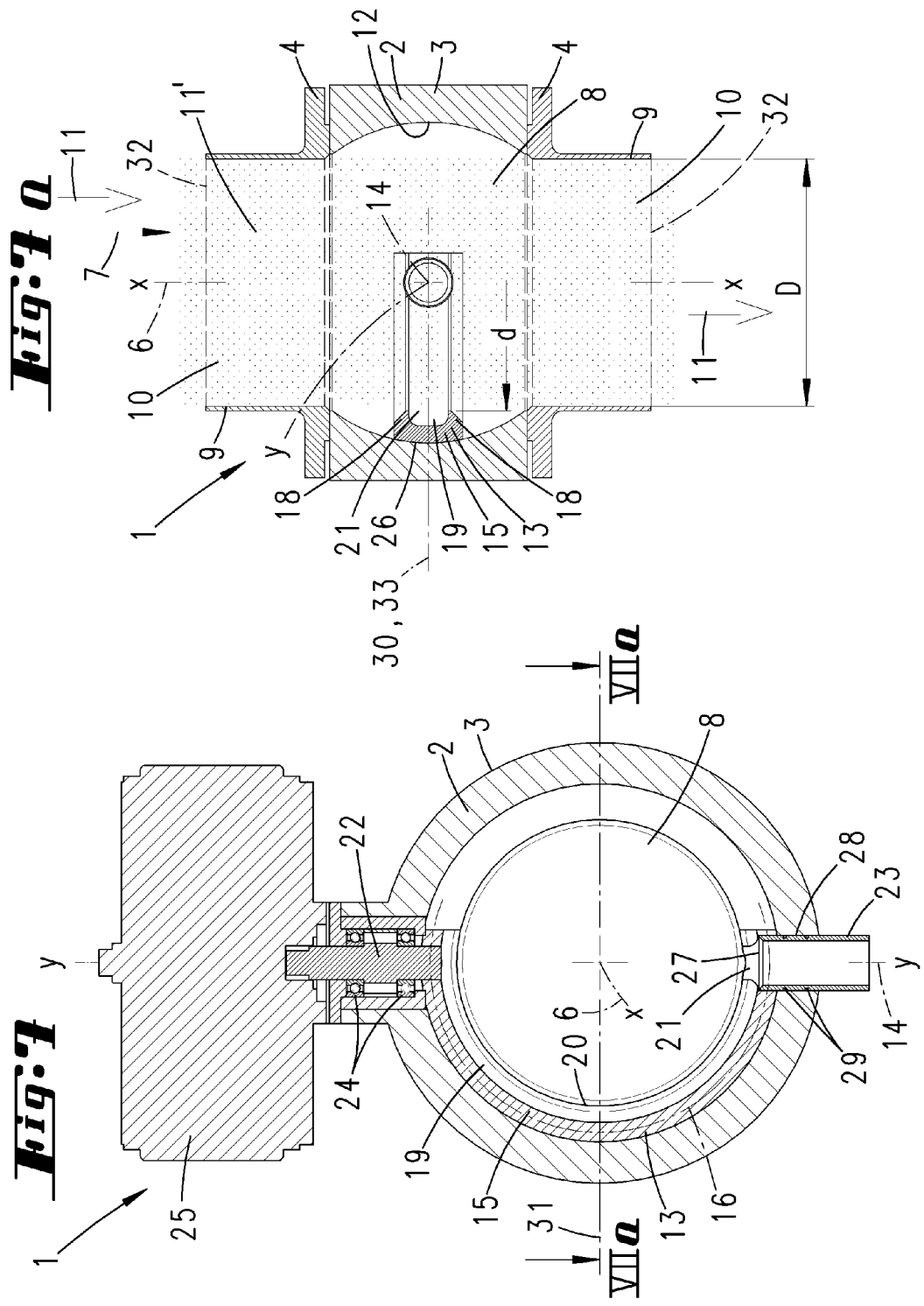

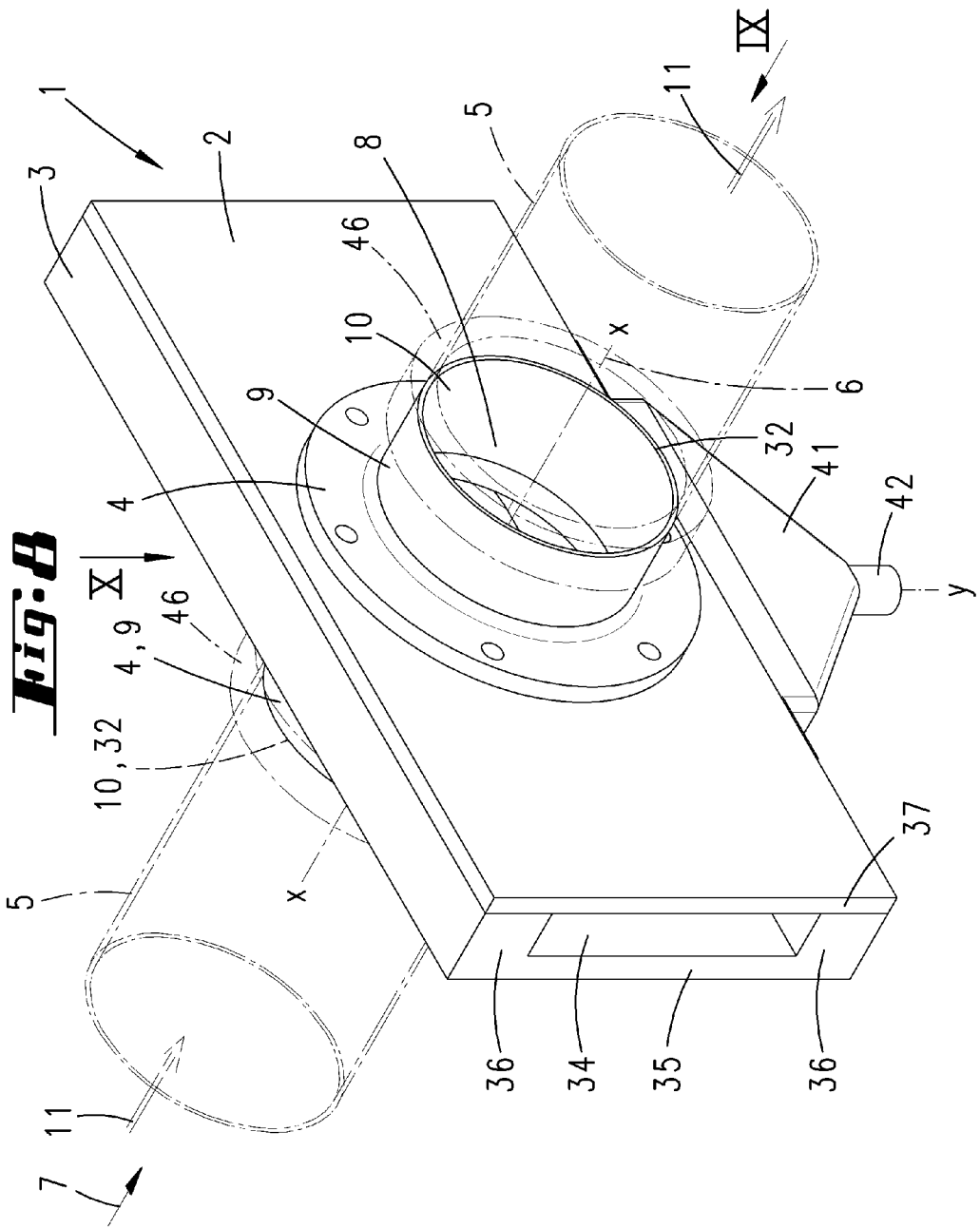

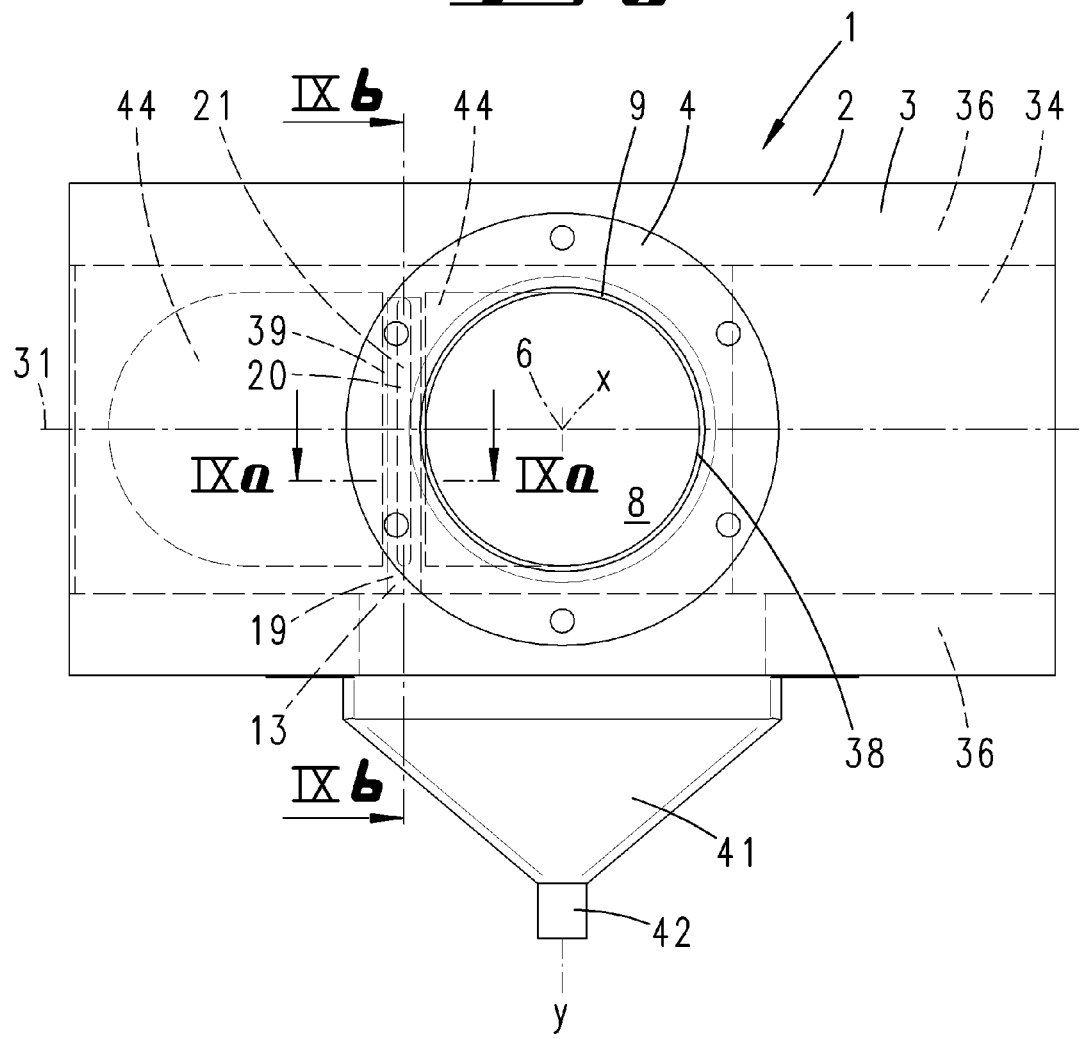

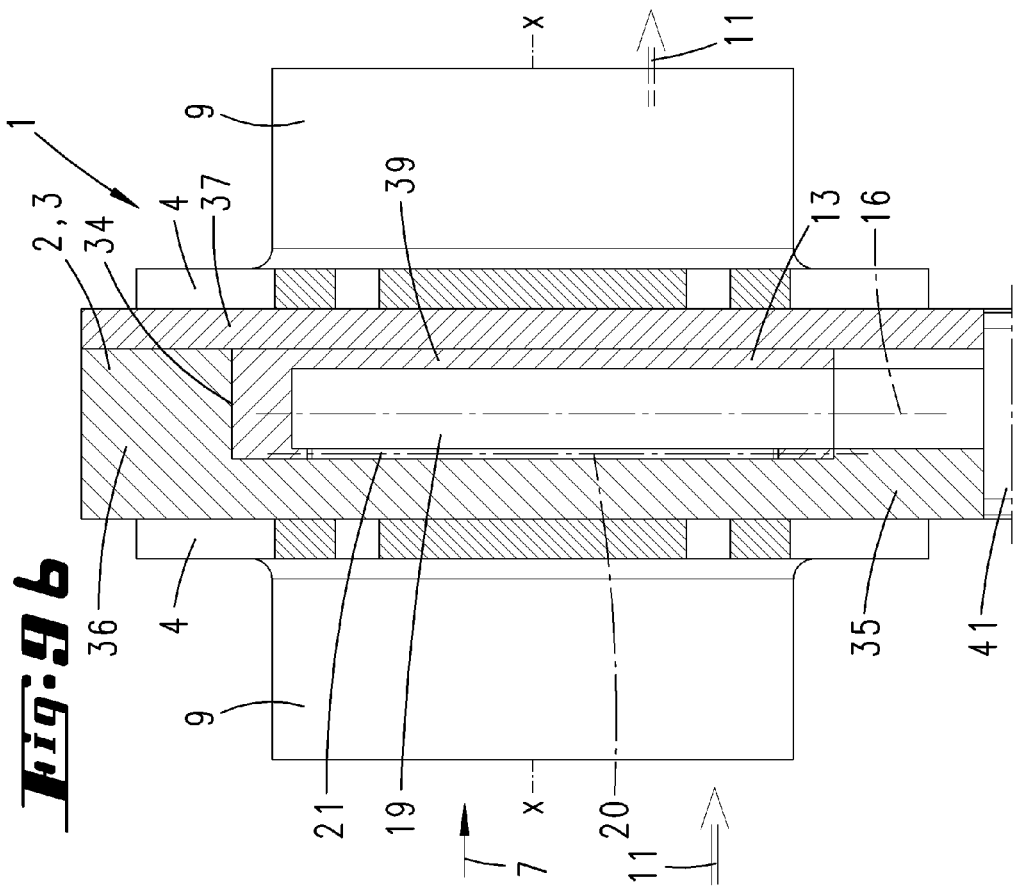
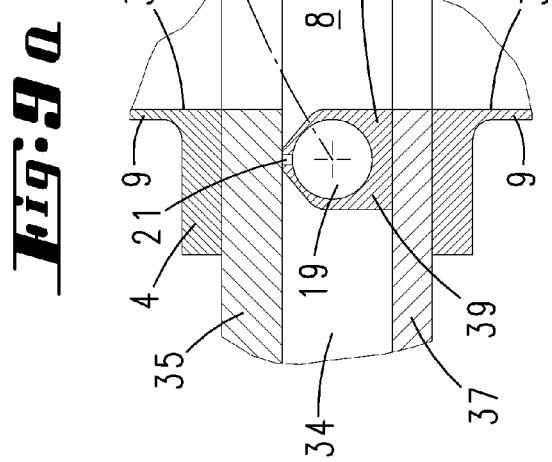

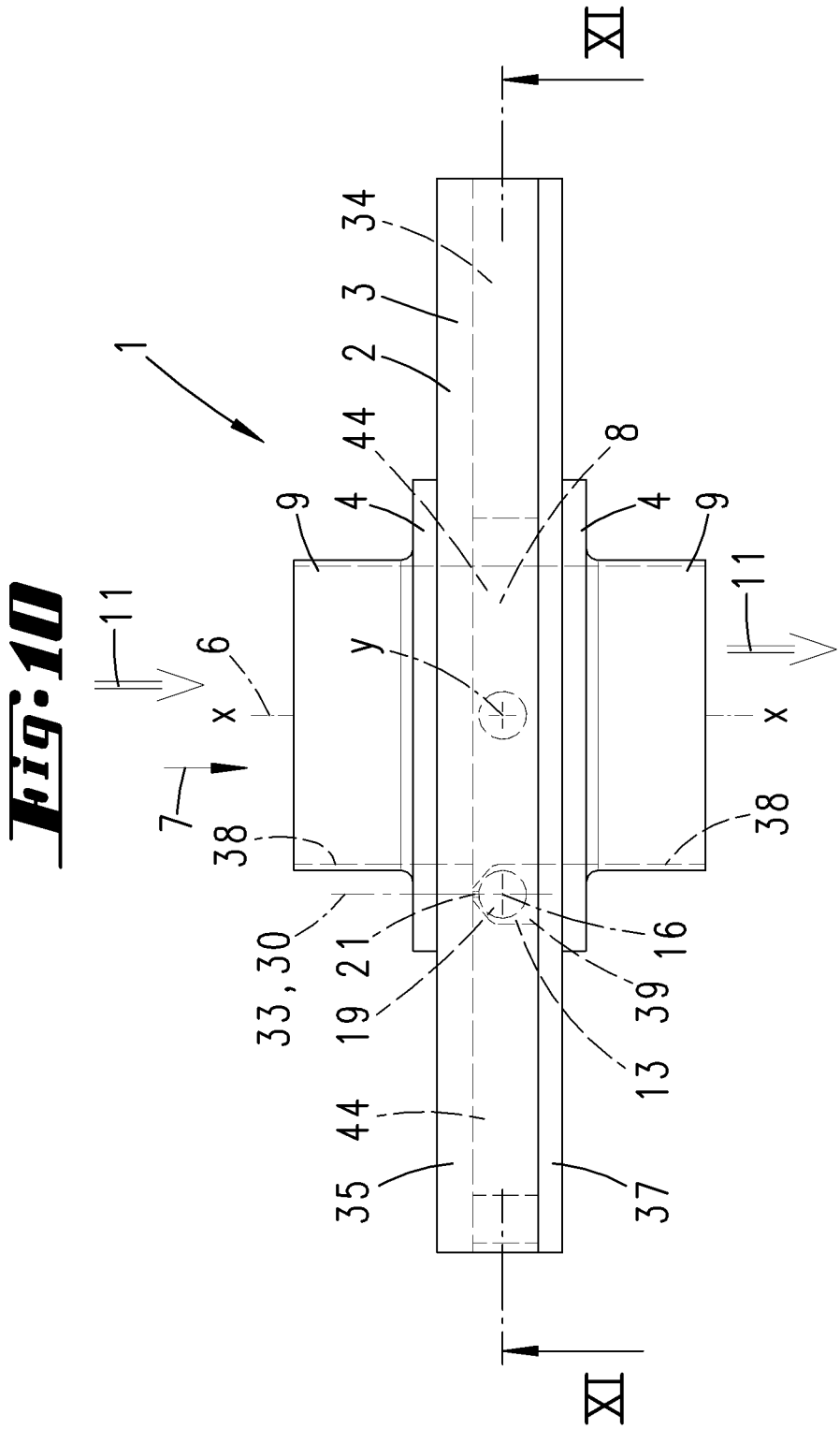

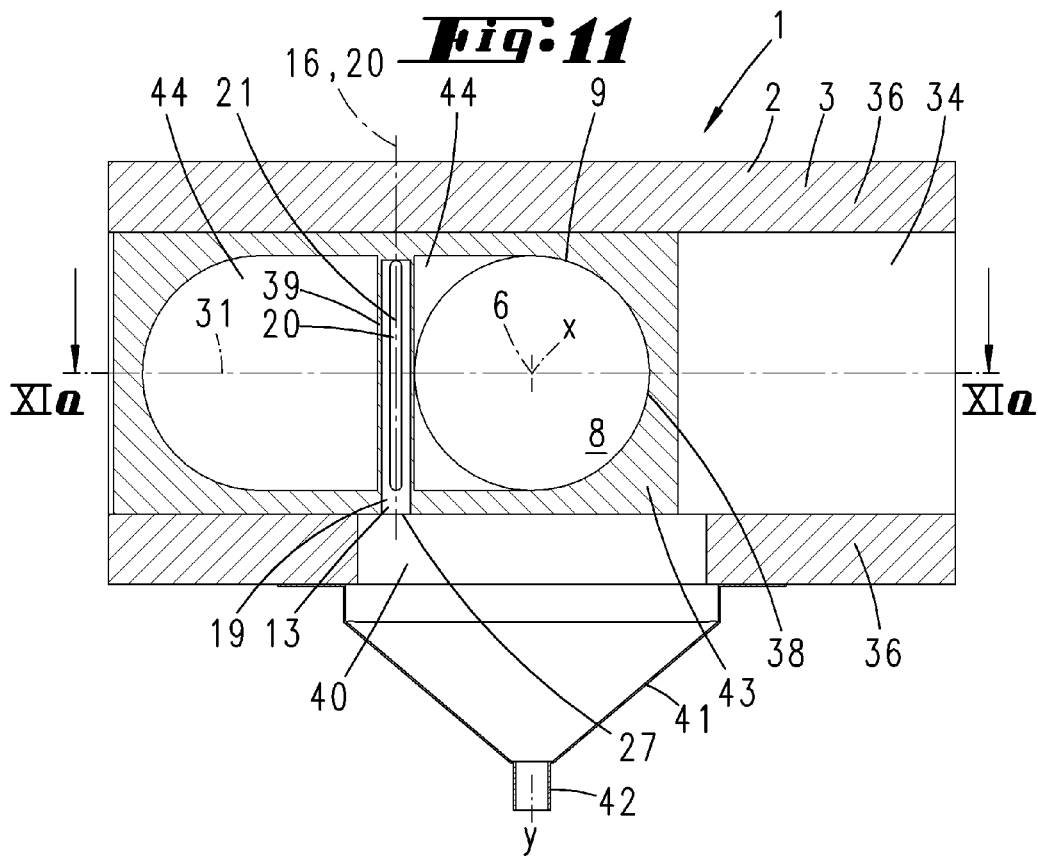
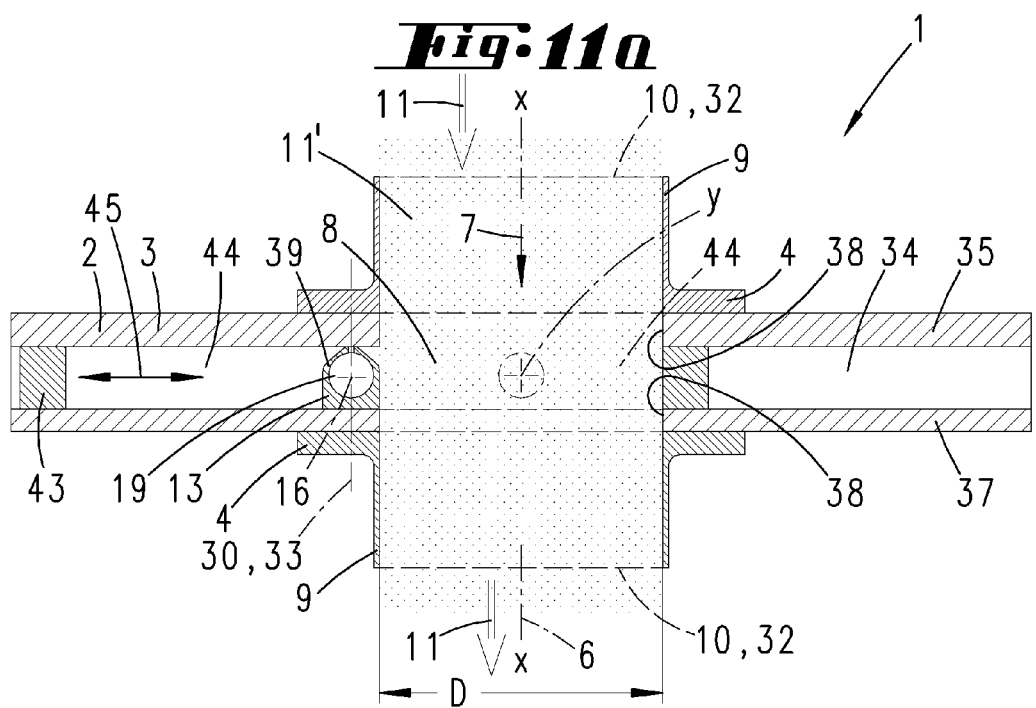

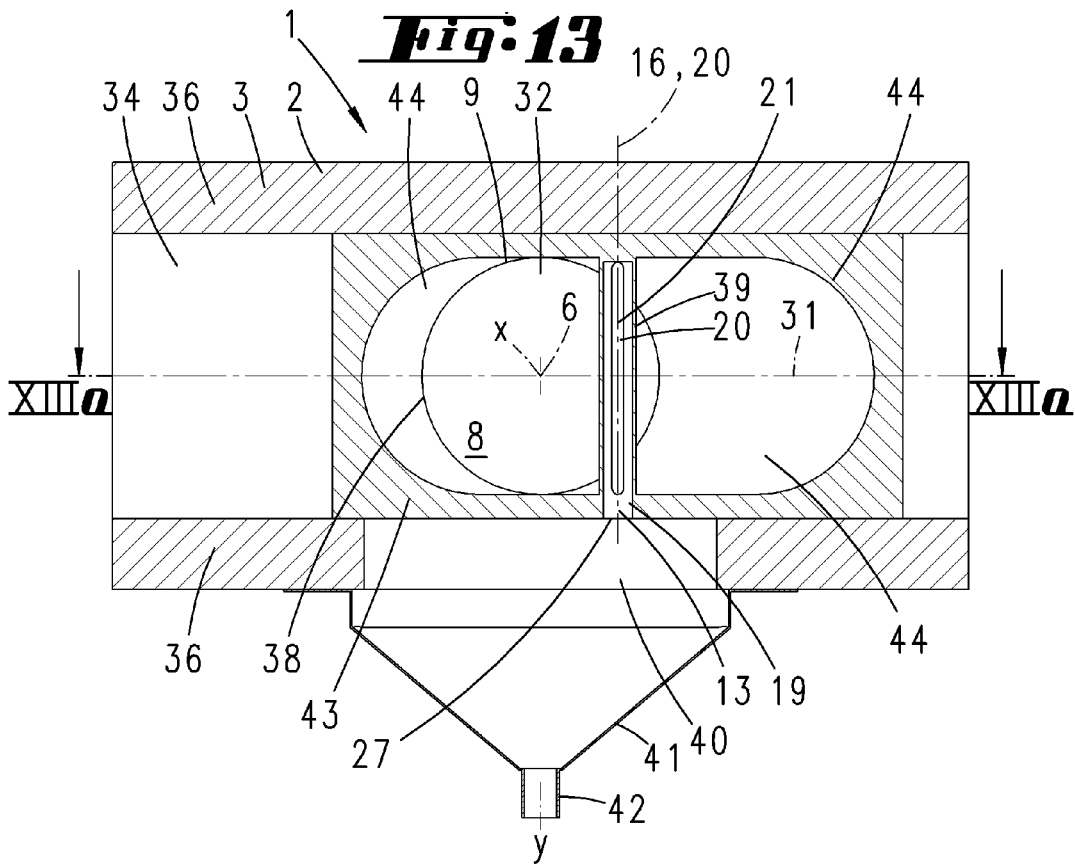
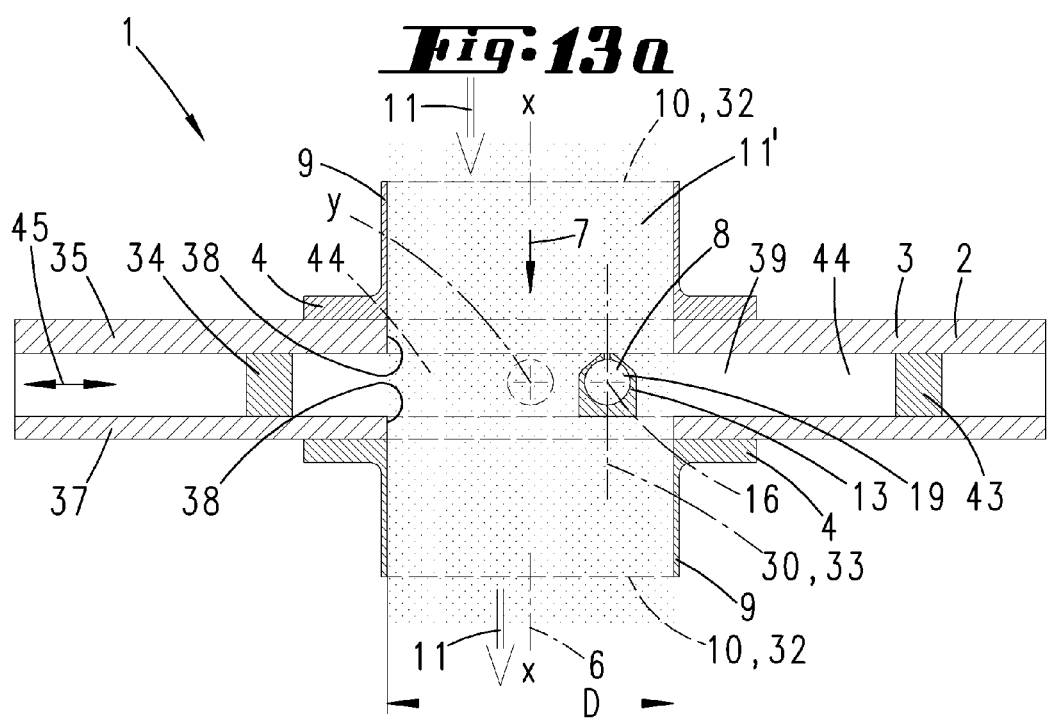

APPARATUS AND METHOD FOR TAKING SAMPLES

The present invention relates, in first instance, to a device for sampling, preferably for withdrawing samples from free-flowing and/or liquid and/or gaseous materials, comprising a housing having an inner housing chamber which has two connection openings, spaced apart from one another, for connecting in each case a line portion through which a material flow may flow, the two connection openings having opening cross-sections which in particular are identical to one another, and the device including a withdrawal element which is movable in the housing chamber, the withdrawal element being formed, at least in portions, in a profile-like manner, the withdrawal element bounding a hollow sampling region, extending along a profile longitudinal direction course, at the periphery of the sampling region, while leaving an entry opening which is preferably slit-like and which extends along an opening longitudinal direction course, guide means being provided by means of which a defined movement pattern of the withdrawal element in the housing chamber is predetermined, along which or as the result of which at least one of the two opening cross-sections in a projection view perpendicular thereto may be traversed over the entire area by means of the entry opening.

Various designs of devices for withdrawing material samples from a material flow which flows through a line or the like are known in the prior art. The known devices generally have funnel-shaped components, and are used in lines in which the material flow is vertically conveyed by gravitation. Such known samplers are not usable in horizontally installed conveying lines having horizontal material flow. In one commonly used design type known from the publications DE 199 09 437 A1, DE 10 2006 049 423 A1, and DD 160 734, a small withdrawal element, also referred to as a so-called sampler, used for sampling, is inserted into a larger downpipe through which material flows, in the transverse direction of the downpipe, in order to withdraw the sample. It is considered to be a limitation that the sample material may be withdrawn only from a limited portion of the flow cross-section, so that a sample that is representative of the flow cross-section according to the so-called theory of sampling (TOS) is not possible.

A sampler is known from DE 197 21 104 A1, the sampling tube of which is fixed in a gimbaled manner in the center of the flow, and the opening of the sampling tube spirally traverses the flow cross-section. However, the limitation here is that the withdrawal element cannot be removed from the material flow; i.e., the withdrawal element disturbs the material flow. A fitting which is also suitable for sampling is known from DD 293 177 A5, by means of which sampling is possible by branching off or temporarily diverting a material flow, so that the regular material flow must be temporarily interrupted. A sampler for withdrawing a representative cross-sectional sample is known from DE 20 2005 009 457 U1, which, however, without further measures does not appear to be suitable for sampling from closed lines. A device of the generic kind is known from DE 101 15 029 B4. The withdrawal element of the device undergoes a conical movement pattern via a drive axis which is inclined with respect to the line longitudinal direction, so that a complicated housing is necessary, and when the flow cross-section is traversed by the withdrawal element, the slitted opening of the withdrawal element is inclined multiaxially with respect to the flow longitudinal direction.

Against this background, it is an object of the invention to advantageously improve a device of the generic kind, so that in particular one or more of the above-mentioned limitations may be at least largely avoided.

The object is achieved according to the invention, in first instance and substantially in conjunction with the features that, as a result of the movement pattern specified by the guide means, an orientation of the withdrawal element in an observation plane which moves with the withdrawal element relative to a geometric intersection line of the observation plane with a nonmoving geometric reference plane which extends perpendicular to the observation plane and to at least one opening cross-section, remains the same when the withdrawal element moves. This type of device is particularly suited for withdrawing samples that are representative of the cross-section of a material flow according to the theory of sampling (TOS), known to those skilled in the art in the field of sampling. Depending on the preferred embodiment, there is the option that during the transverse movement through the material flow, i.e., over the opening cross-section or flow cross-section, the inclination of the withdrawal element or the entry opening thereof with respect to the flow longitudinal direction of the material flow does not change, or changes only in one direction or one plane, for example. Largely identical sampling conditions are thus provided over the entire opening cross-section or flow cross-section. In addition, there is the option to accommodate this type of movement pattern in a compact, simple housing. A device within the scope of the invention which also includes the aspects explained below may be used, for example, for sampling a material flow which may contain one or more of practically any materials or media that are pourable and/or flowable. For example, the device may be used for withdrawing samples from powder, ash, pellets, granules, or suspended liquids; sampling of gases is also conceivable. In addition, depending on the requirements, a device according to the invention may have practically any desired dimensions. The term "withdrawal element" is used synonymously with the term "sampler." The profile longitudinal direction course of the withdrawal element is understood to mean the shape or course thereof in the profile direction, i.e., transverse to the profile cross-section, where the profile longitudinal direction course may refer to the center of the cross-section or to the center of gravity of the cross-section, for example. It is preferred that the profile longitudinal direction course extends within a geometric plane. Similarly, the opening longitudinal direction course is understood to mean the shape of the course of the elongated entry opening transverse to the profile cross-section or opening cross-section, i.e., in the opening longitudinal direction or profile longitudinal direction. The device according to the invention is preferably installed in a line through which the material flow or material passes, in a manner or direction such that the elongated entry opening is inclined diametrically and/or in a plane with respect to the line longitudinal direction during the movement of the withdrawal element or collection vessel, so that materials or goods flowing through the housing transversely with respect to the connection opening impact on the entry opening and are able to pass through same and into the hollow sampling region of the withdrawal element, and from there to exit the sampler, preferably through an exit opening. It is understood that, if necessary, a device according to the invention may also be modified in such a way that the elongated entry opening traverses only a portion, not all, of the area of the flow cross-section during sampling. In an advantageous refinement or use, the connection openings are connected to one line portion each, the direction of longitudinal extent of one or both line portions being oriented horizontally or at least substantially horizontally. An important feature is that the invention is capable of, i.e., the device according to the invention is suitable for, withdrawing a representative cross-sectional sample not only from a vertical material flow, but also selectively from a horizontal material flow, for example. In addition, for the invention it is not important in which direction a material flow "flows" in the horizontal and/or vertical line.

Within the scope of the present invention, this feature may also be important on its own. In this regard, according to a second aspect the invention relates to a device for sampling, preferably for withdrawing samples from free-flowing and/or liquid and/or gaseous material, comprising a housing having an inner housing chamber which has two connection openings, spaced apart from one another, for connecting in each case a line portion through which a material flow may flow, the two connection openings having opening cross-sections which are preferably identical to one another, and the device including a withdrawal element which is movable in the housing chamber, the withdrawal element being formed, at least in portions, in a profile-like manner, and the withdrawal element bounding a hollow sampling region, extending along a profile longitudinal direction course, at the periphery of the sampling region, while leaving an entry opening, which is preferably slit-like and which extends along an opening longitudinal direction course, and guide means being provided by means of which a defined movement pattern of the withdrawal element in the housing chamber is predetermined. For an advantageous refinement it is proposed that a line portion is connected to each of the two connection openings, from which one line portion extends horizontally or substantially horizontally, or from which both line portions extend horizontally or substantially horizontally.

With regard to the aspects of the invention explained above and hereinafter, there are numerous options for preferred refinement, which, however, may also be independently important within the scope of the invention, i.e., without the features of claims 1 and 3. Thus, there is the option that the opening longitudinal direction course of the withdrawal element extends geometrically along a straight line, and that a movement path or movement direction of the withdrawal element extends geometrically along a straight line oriented transversely with respect to the opening longitudinal direction course.

Within the scope of the invention, these features may also be important independently, or also alone in conjunction with the features of the generic kind of the second aspect of the invention, i.e., claim 3. Alternatively, there is the option that the opening longitudinal direction course of the withdrawal element extends, preferably in an even manner, along a geometric spherical surface, and that a movement path or a movement pattern of the withdrawal element extends geometrically in a circular direction about a rotational axis. According to another aspect, within the scope of the invention these features may also be important, independently on their own, or also alone in conjunction with the features of the generic kind of the second aspect of the invention, i.e., claim 3. In particular in conjunction with these features, it is preferred that a back surface of the withdrawal element facing away from the entry surface extends longitudinally and transversely with respect to the opening longitudinal direction course along a spherical surface, and that the housing chamber has an inner wall portion between the two connection openings which extends along a geometric spherical surface and conforms without play, or at least with little play, to the surface of the withdrawal element during at least a portion of its movement. In addition, articulating means may be connected to one or both lengthwise ends of the withdrawal element, which together with articulating means of the housing form a pivot joint about a rotational axis in a geometric plane defined by the profile longitudinal direction course.

According to a further concept which within the scope of the present invention may likewise be important as a preferred refinement as well as independently on its own, there is the option that the withdrawal element, preferably at two possible opposite positions, may be completely moved, within its movement path in a projection view in each case perpendicular to the opening cross-sections, out of an overlap with one opening cross-section or with both opening cross-sections. For this purpose, the housing chamber may include one or more receiving cavities in its interior which, in a projection view in the material flow longitudinal direction, adjoin in an open manner the outer edge of the opening cross-section or flow cross-section, and into which the sampler may preferably be completely retracted when no sample is to be withdrawn, so that the sampler does not protrude in an interfering manner into the flow core cross-section specified by the connection openings. Disturbance of the material flow by the withdrawal element outside the sampling periods may thus be avoided.

It is also preferred that the withdrawal element has a grooved shape or is formed as an elongated hollow body that is slitted along its opening longitudinal direction course, preferably as a slitted tube-like hollow body, at at least one lengthwise end of which an exit opening, preferably closed along its entire periphery, for the sample material, is formed. It is considered to be advantageous that the hollow sampling region, at the end face of one of its lengthwise ends, merges into the exit opening, and that the exit opening points downwardly in the selected configuration or position of the sampler. The material sample may thus also exit from the withdrawal element with gravity assistance, i.e., optionally also independently of a flow positive pressure for assisting in the sample discharge. Depending on the requirements, the sample material may be discharged either continuously during the sampling or discontinuously after completion of the sampling. To achieve sampling that is representative of the cross-section, during a collection operation the flow cross-section may be traversed by the entry opening of the withdrawal element in a projection view, preferably one or more times over the entire area. If in particular continuous sample discharge is provided, this also allows multiple cross-sectional traversals by the withdrawal element over a collection period of any desired length.

There are various options for embodying the withdrawal element or sampler, which may depart from the rotatable or linearly movable embodiments described by way of example here and also hereinafter with reference to the figures. Depending on the application, the sampling element may be formed differently according to the requirements of the theory of sampling (TOS). The parameters in this regard are in particular the particle size of the sample material, the diameters or cross-sectional dimensions of the withdrawal element and the diameters of the connection openings in the housing, the mass throughput and the speed, as well as the material itself (for example, suspended liquids, powdered materials, granules, and other solids which may be conducted through pipes). These input parameters must be taken into account in the design of the withdrawal element or sampler and the device. Other influencing variables for the specific embodiment may be the pressure and the material flow rate, as well as the cohesion tendency of material particles, for example.

Advantages of the device according to the invention are that the device is particularly suitable for sampling, according to TOS, which is representative of the entire flow cross-section, that placement in horizontal line portions, among others, is also possible, that the material flow does not have to interrupted for sampling, and that in a preferred embodiment the withdrawal element, which is used for collecting and conducting away sample material, may also be moved outside the flow core cross-section of the line when no sample is to be withdrawn. The housing of the device may be easily flanged in, for example into the line of a material flow.

There is also the option that the hollow sampling region used for collecting sample material from the flow is unbounded, i.e., open, on approximately one side at its cross-section that is oriented transversely with respect to the longitudinal direction course. In this regard, a groove-shaped design may be present. Alternatively, at its cross-section that is oriented transversely with respect to the longitudinal direction course, for example, the hollow sampling region may have only one (or a plurality of) narrow wall interruption(s), so that more than one hollow body having a longitudinal slit is involved. The width of the entry opening in the longitudinal direction may be constant or variable. In particular, there is the option that the width of the entry opening transverse to the opening longitudinal direction course and/or the width of the cross-section of the hollow sampling region transverse to the profile longitudinal direction course is/are continuous, or constant at least in portions, and is/are smaller than the maximum extent, preferably smaller than the diameter, of the free opening cross-section of the connection openings.

The length of the entry opening preferably corresponds to at least the maximum extent of at least one of the two opening cross-sections in at least one of the cross-sectional directions, and preferably corresponds at least to the diameter of the free opening cross-section.

It is considered advantageous that, in an observation plane defined by the profile longitudinal direction course of the withdrawal element together with a geometric longitudinal center line extending centrally and transversely through an opening cross-section, the profile longitudinal direction course and/or the opening longitudinal direction course extend(s) point-symmetrically with respect to its/their intersecting point with the longitudinal center line, and preferably axially symmetrically with respect to the longitudinal center line. This likewise has a favorable effect on desired sampling that is representative of the cross-section. With regard to the opening cross-sections of the two connection openings, it is preferred that they are situated parallel to one another at a distance from one another on the housing, and situated concentrically with respect to one another in a projection direction perpendicular to their cross-sectional planes. This allows a material flow straight through the housing, and favors the formation of a flow having the most uniform flow and sampling conditions possible over the flow cross-section. Furthermore, it is preferred that the movement direction of the withdrawal element is oriented transversely, preferably perpendicularly, with respect to the opening longitudinal direction course of the withdrawal element or of the hollow sampling region. The withdrawal element may, for example, be moved manually or by means of a drive device which in particular is automated. For example, an electric, pneumatic, or hydraulic drive or the like may preferably be provided for the movement drive of the withdrawal element in the housing chamber, the drive device being adapted to a movement of the withdrawal element preferably at a constant speed. The so-called withdrawal element described herein, which is also referred to as a so-called sampler in technical usage, may have a one- or multipart design.

According to another aspect, the invention further relates to a method for sampling, preferably for withdrawing samples from free-flowing and/or liquid and/or gaseous material, comprising the following method steps: providing a device for sampling, comprising a housing having an inner housing chamber which has two connection openings, spaced apart from one another, for connecting in each case a line portion through which a material flow may flow, the two connection openings preferably having identical opening cross-sections, and the device including a withdrawal element which is movable in the housing chamber, the withdrawal element being formed, at least in portions, in a profile-like manner, the withdrawal element bounding a hollow sampling region, extending along a profile longitudinal direction course, at the periphery of the sampling region, while leaving an entry opening which is preferably slit-like and which extends along an opening longitudinal direction course, and guide means being provided by means of which a defined movement pattern or movement path of the withdrawal element in the housing chamber is predetermined, along which at least one of the two opening cross-sections in a projection view perpendicular thereto may be traversed over the entire area by means of the entry opening. For an advantageous refinement, the invention proposes that while a material flow is conducted through the housing chamber by means of the two connection openings, the withdrawal element is moved through the housing chamber, so that the orientation of the withdrawal element in an observation plane which moves with the withdrawal element relative to a geometric intersection line of the observation plane with a nonmoving geometric reference plane which extends perpendicular to the observation plane and to at least one opening cross-section, remains the same when the withdrawal element is moved. With regard to the effects and advantages that are achievable in this respect, reference is made to the preceding description. There is the advantageous option that the device used in the method has one or more of the above-described features.

Figure 12:
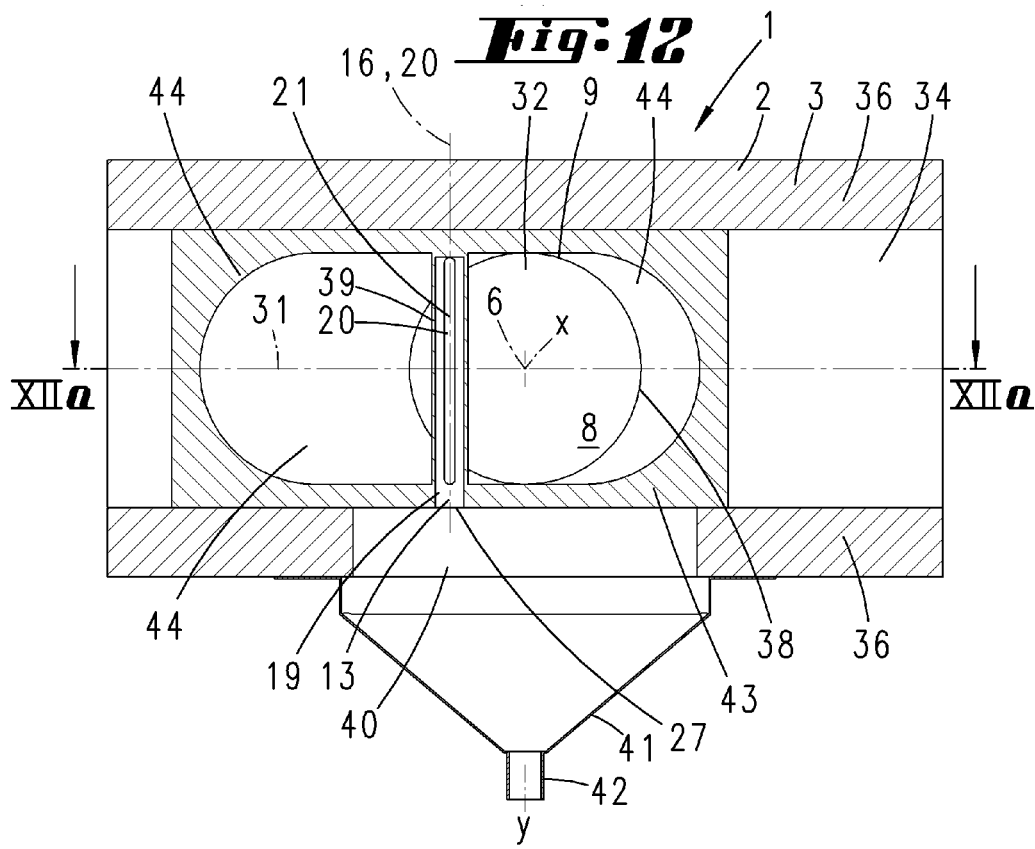
Figure 12A:
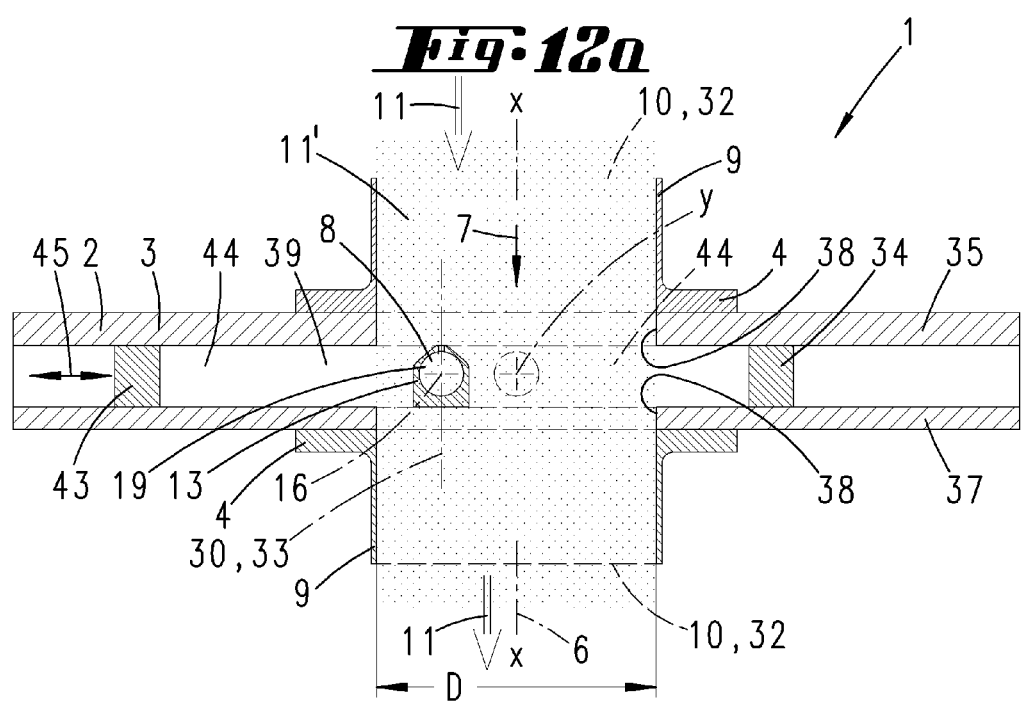
Figure 14:
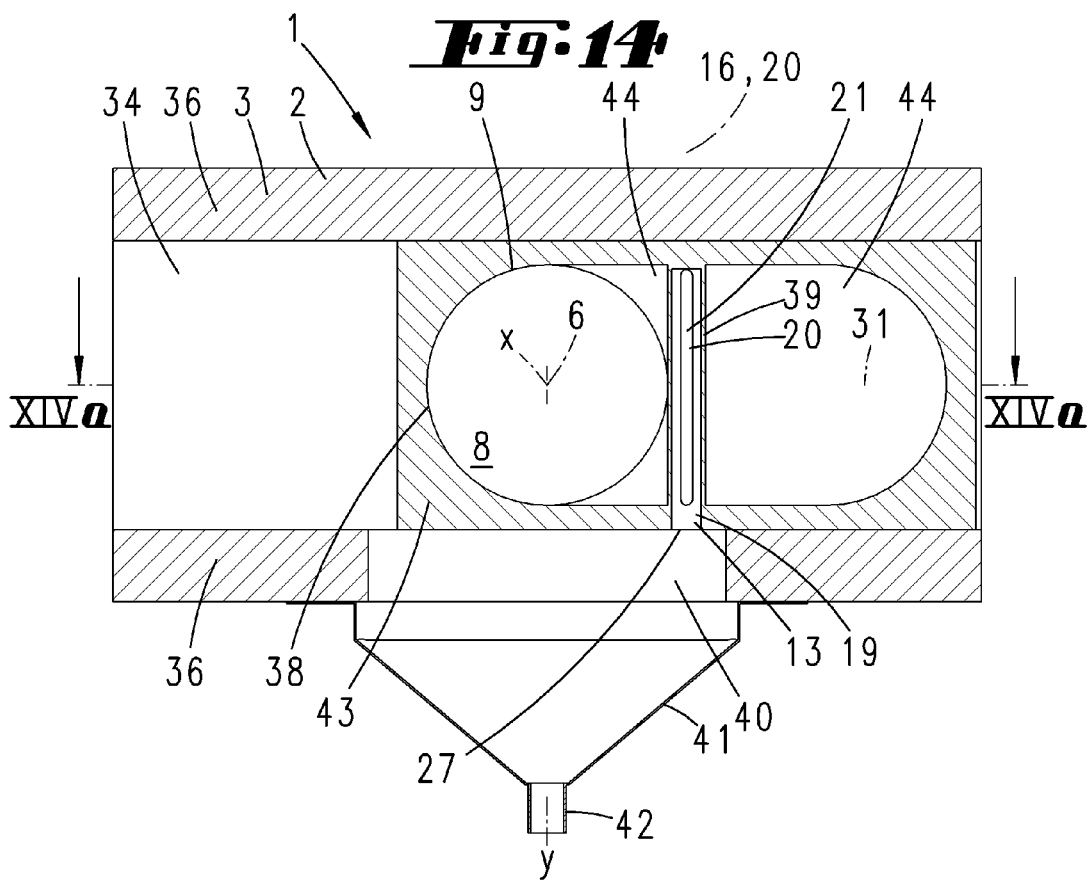
Figure 14A:
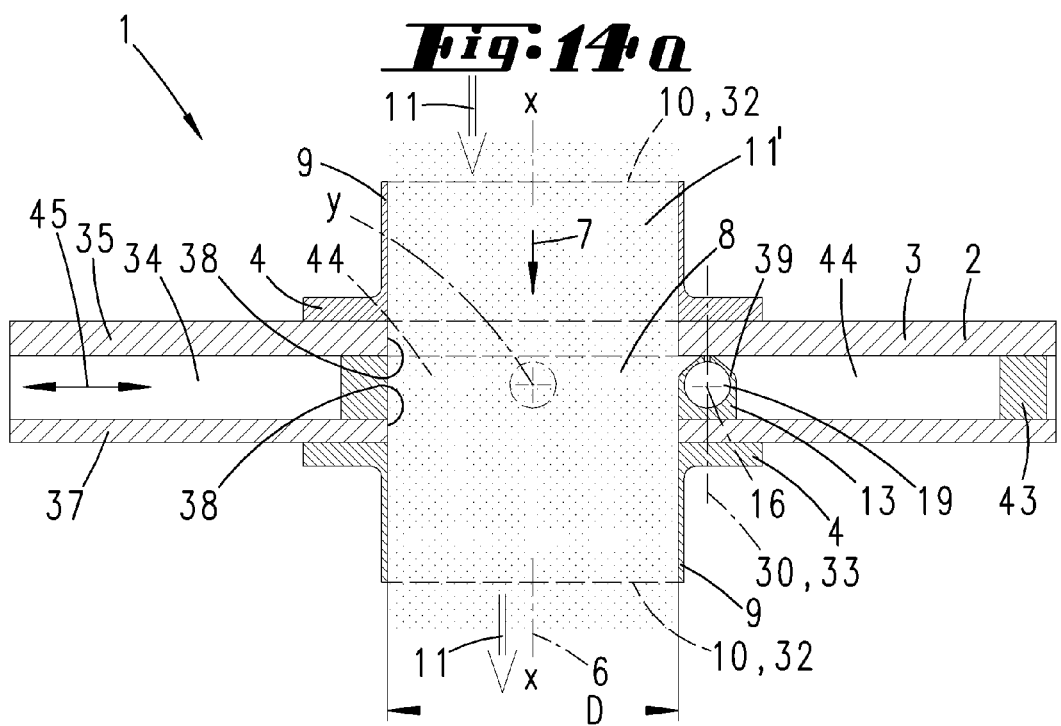

The invention is described in greater detail below with reference to the appended figures which illustrate preferred exemplary embodiments. The figures show the following:

FIG. 1 shows a perspective view of a device according to the invention for sampling according to a first preferred exemplary embodiment, situated between two line portions indicated by dashed lines, FIG. 2 shows the device according to FIG. 1 in the viewing direction II therein, FIG. 3 shows the device according to FIG. 1 in the viewing direction III therein, FIG. 4 shows a perspective view of the device according to FIGS. 1 to 3, but in an enlarged and partially cutaway view, FIG. 5 shows a sectional view in reduced scale of the arrangement from FIG. 4 along the section plane VV therein, with a corresponding rotational position of the withdrawal element, FIG. 5a shows a sectional view of the arrangement according to FIG. 5 along the section plane Va-Va therein, FIG. 6 shows a sectional view analogous to FIG. 5, but with the withdrawal element rotationally displaced, for purposes of illustration the withdrawal element being sectioned above the plane of the drawing, FIG. 6a shows a sectional view of the arrangement from FIG. 6 along the section plane VIa-VIa therein, FIG. 7 shows a sectional view analogous to FIGS. 5, 6, but with the withdrawal element further rotationally displaced, FIG. 7a shows a sectional view of the arrangement from FIG. 7 along the section plane VIIa-VIIa therein, FIG. 8 shows a perspective view of a device according to the invention according to a second preferred exemplary embodiment, situated between two line FIG. 9 shows the arrangement from FIG. 8 in the viewing direction IX therein, FIG. 9a shows a partial section along the section line IXa-IXa from FIG. 9, FIG. 9b shows a partial section along the section line IXb-IXb from FIG. 9, FIG. 10 shows the device according to FIG. 8 in the viewing direction X therein, FIG. 11 shows a sectional view of the device from FIG. 10 along the section plane XI-XI therein, with the withdrawal element in a first position, FIG. 11a shows a sectional view of the situation in FIG. 11 along the section plane XIa-XIa therein, FIG. 12 shows a sectional view analogous to FIG. 11, with the withdrawal element in a second position, FIG. 12a shows a sectional view of the situation from FIG. 12 along the section plane XIIa-XIIa therein, FIG. 13 shows a sectional view analogous to FIGS. 11, 12, but with the withdrawal element in a third position, FIG. 13a shows the situation from FIG. 13 along the section plane XIIIa-XIIIa therein, FIG. 14 shows a sectional view analogous to FIGS. 11 to 13, but with the withdrawal element in a fourth position, and FIG. 14a shows the situation from FIG. 14 along the section plane XIVa-XIVa therein.

With reference to FIGS. 1 to 7a, in first instance a device 1 according to the invention for sampling, according to a first preferred exemplary embodiment, is described. This device comprises a housing 2, which in the example (i.e., not necessarily) has a multipart design with a central housing body 3 and two pipe flanges 4, each screwed to one of the two opposite end faces of the housing body 3. The pipe flanges 4 in each case are used for securing a line portion 5, which in FIG. 1 is indicated by dashed lines in a longitudinal portion. The geometric center axis xx of the pipe flanges thus describes the direction of longitudinal extent 6, i.e., the flow longitudinal direction, of a line in which the device 1 has been inserted in order to withdraw material samples from a material flow 11 indicated by arrows in FIG. 1, which flows in the flow direction 7 indicated by the arrow in FIG. 1. The interior of the housing 2 forms a housing chamber 8 having two connection openings 10 situated parallel to one another at a distance from one another in the direction of longitudinal extent 6 and formed by the flange pieces 9. The connection openings have the same diameter D, are in alignment with one another, and thus specify a certain core cross-section for the material flow 11, schematically indicated by dots, only in this flow core area 11' in FIGS. 5a to 7a. However, it is understood that, depending on the flow conditions, the flowing material occupies the entire housing chamber 8, i.e., also the edge regions extending around the geometric center line xx and adjoining the concave inner wall portion 12, except that, strictly for illustrating the flow core cross-section, the dot pattern is not present there. In the exemplary embodiment, a withdrawal element 13, which is also referred to as a sampler in technical usage, is situated within the housing 2 so as to be rotatable about a geometric rotational axis 14 which extends along the coordinate axis y-y. As illustrated in particular in FIGS. 4 and 5, in the example the withdrawal element 13 includes a profile-like groove 15. The profile longitudinal direction course 16 which extends centrally in the transverse direction through the groove cross-section shown in FIG. 4, for example, extends along a circular line over slightly more than one-half of a lateral circumference (see FIG. 5). The groove base 17 and the two groove walls 18 bound a hollow sampling region 19, extending in a U-profile manner along the profile longitudinal direction course 16, so that the hollow sampling region has an entry opening 21 for sample material which is bounded in parallel by the two groove walls 18 and which extends along a central opening longitudinal direction course 20 which is central with respect to the groove walls. The surfaces of the groove 15 facing the central opening longitudinal direction course form a collection surface for sample material. As a result, the opening longitudinal direction course 20 also extends along an imaginary circular line in the projection view according to FIG. 5, likewise over approximately more than one-half of the lateral circumference; in the example shown, the circumferential angle is between approximately 200° and 210°. Depending on the rotational position of the withdrawal element 13, the entry opening of the sampling region 19 more or less faces the flow longitudinal direction 7 of the material flow; as illustrated in FIGS. 5a to 7a, the movement path or movement direction of the groove 15 extends in a circular direction about the rotational axis 14. A pivot pin 22, 23 which is concentric with respect to the rotational axis 14 is secured in the region of each of the two lengthwise ends of the groove 15. Both pivot pins 22, 23 are fixedly inserted into holes in the groove base 17 (for example, welded there), and extend only radially outwardly with respect to the approximately semicircular or sickle-like shape of the groove, so that the pivot pins 22, 23 do not protrude into the sampling region 19 which is used for collecting and conducting away sample material. The upper pivot pin 22 in the viewing direction in FIG. 5 is mounted at the top side of the housing 2 by means of ball bearings 24. The opposite, i.e., top, end of the pivot pin is connected in a rotationally form-locked manner to a drive 25, only schematically indicated, which may be an electric motor or a pneumatic or hydraulic drive, for example. When the drive 25 is activated, it transmits a torque to the groove 15 via the pivot pin 22, so that the groove undergoes a rotating motion about the geometric rotational axis 14. In the example, it is provided that a convex surface 26 of the groove 15 on the rear side, facing away from the entry opening 21, viewed longitudinally and transversely with respect to the profile longitudinal direction course 16, extends along an imaginary spherical surface, and that the concave inner wall portion 12 of the housing 2 likewise extends along an imaginary spherical surface having practically the same spherical diameter, so that during the rotating motion, the surface 26 of the groove 15 conforms, practically free of play, to the inner wall portion 12. In the example there is no rotational stop, so that the withdrawal element may rotate about its rotational axis without limitation. Thus, for the withdrawal of samples the device 1 is not restricted to the flow direction 7 shown in FIG. 1. Rather, if the flow direction 7 is reversed, the device may also be adapted thereto by rotating the sampler, i.e., the withdrawal element 13, by one-half revolution for the changeover. The lower pivot pin 23 for the withdrawal element 13 in the viewing direction in FIGS. 4, 5 is formed as a cylindrical sleeve, and the lowermost portion of the hollow sampling region 19 merges into the hollow sleeve interior in an exit opening 27. This allows material (powder, granules, or the like) which impacts on the inner wall of the groove 15 in the flow direction 7 to be transported along the groove base 17 in the groove longitudinal direction, and to be removed from the withdrawal element 13, and thus from the device 1, through the exit opening 27 and through the hollow pivot pin 23. The lower sleeve 23 is held in a hole 28 through the lower apex of the housing body 3 so as to be rotatable about the rotational axis 14, and is sealed therein by means of two O-rings 29. The pivot pins 22, 23 together with the ball bearings 24 and the hole 28 thus form guide means, by means of which a defined movement pattern of the withdrawal element 13 is predetermined as rotation about the rotational axis 14 in the housing chamber 8.

FIGS. 5a to 7a illustrate that, although during a rotation the entry opening 21 in the groove 15 assumes various angles of inclination with respect to the upper, facing opening cross-section 32 in FIGS. 5a, 6a, 7a, as a result of the rotation, the entire area of this opening cross-section 32 (diameter D) of the connection opening 10 which forms the housing entry may be traversed in a projection view in the flow longitudinal direction 7, i.e., perpendicular to the opening cross-sections 32, by means of the entry opening 21. As a result of the movement pattern specified by the guide means, the orientation of the withdrawal element 13 in an observation plane 30, which is rotated with the withdrawal element about the rotational axis 14, relative to the geometric intersection line 33 of the observation plane with a nonmoving geometric reference plane 31 which extends perpendicular to the observation plane 30 and to the opening cross-section 32, is unchanged when the withdrawal element 13 moves. In the example, the reference plane 31 extends horizontally through the direction of longitudinal extent 6, i.e., perpendicularly with respect to the geometric rotational axis 14. The observation plane 30 is defined by the profile longitudinal direction course 16 and likewise by the opening longitudinal direction course 20. The observation plane thus extends perpendicularly with respect to the plane of the drawing in FIG. 5a. Within the observation plane 30, the withdrawal element 30 [sic; 13] also in particular does not change its angular orientation with respect to the reference plane 31 which intersects the observation plane 30, so that in this regard the same conditions are always present for the sampling, regardless of the position of the groove 15 in the housing chamber 8. In order to carry out a single complete traversal of the upper opening cross-section 32, in the viewing direction in FIGS. 5a, 6a, and 7a, by the entry opening 21 in the groove 15 which faces the opening cross-section in the projection view, the withdrawal element 13 may be rotated at least once from its lateral position shown in FIG. 5a, in which the observation plane 30 is perpendicular to the flow direction 7, i.e., parallel to the opening cross-sections, by one-half revolution, and thus into the edge position shown in FIG. 7a. FIG. 6a shows an intermediate rotational position. Thus, during this movement, material for the sample is withdrawn from the material flow from any part of the flow cross-section schematically denoted by the dot pattern, by way of the groove 15. In the projection view, during the movement, every portion of the upper opening cross-section 32 temporarily oppositely faces at least a portion of the entry opening 21 in the groove 15. On the other hand, FIGS. 5a and 7a also show that the withdrawal element 13 may be completely moved out of overlap with the opening cross-sections 32, in the two edge positions in which the observation plane 30 defined by the profile longitudinal direction course 16 is oriented perpendicularly with respect to the flow direction 7. The groove 15, and in this respect the entire withdrawal element 13, are there situated outside the flow core cross-section indicated by the dot pattern. To this end, it is provided that the diameter d of a circular line along which the free edges of the groove walls 18 extend is equal to or greater than the diameter D of the connection openings 10. In this regard, in the reference plane 31 (which coincides with the plane of the drawing in FIGS. 5a, 6a, and 7a), the concave inner wall portion 12 forms a receiving area, in the static flow zone in a manner of speaking, for the withdrawal element 13 on both sides of the core flow. Since the pivot pins 22, 23 also do not protrude inwardly, in the rotational positions shown in FIGS. 5a and 7a, the core flow or main flow is not disturbed, or in any event is not significantly disturbed. The line portions 5 indicated by dashed lines in FIG. 1 each have the same inner and outer diameter as the flange pieces 9, are in flush abutment with the respective flange pieces 9, and are each tightly connected to the respective flange pieces 9 via a suitable pipe connector 46. In the example, the pipe connector 46 is a short pipe section whose inner diameter corresponds to the outer diameter of the flange piece 9 and of the line portion 5, and which is pushed in the longitudinal direction onto the flange pieces 9 and the line portion 5 in an overlapping manner, and in each case is peripherally secured thereto (for example, glued, welded, or the like). It is understood that there are also alternative options for securing line portions 5.

A second preferred exemplary embodiment of a device 1 according to the invention for sampling is described with reference to FIGS. 8 to 14a. For a simpler overview and better understanding, details which structurally or functionally correspond to the preceding example are provided with the same reference numerals. As described in greater detail below, in this exemplary embodiment, the movement of the withdrawal element 13 is translational, not rotational. Here as well, the device 1 comprises a multipart housing 2. A housing body 3 basically has a flat, U profile-like cross-section. The housing body 3 shown may be made, for example, from a rectangular metal plate into which a recess 34, having a rectangular cross-section and running on a plate surface in the longitudinal direction thereof, is introduced as part of the housing chamber 8. A rectangular, large-surface housing wall 35 thus remains, along the longitudinal edges of which two wall projections 36 extend parallel to one another. A second housing wall 37 is sealingly secured or screwed to the wall projections. Through holes 38 which are mutually aligned, i.e., situated concentrically with respect to the longitudinal center line x-x, are provided through the housing walls 35 and 37. The housing 2 also includes two pipe flanges 4 which in each case are externally secured, concentrically with respect to the longitudinal center line x-x, to the housing walls 35, 37 on either side. The connection openings 10 of the pipe flanges are situated parallel to one another at a distance from one another and have the same circular opening cross-section 32 with diameter D. A withdrawal element 13, i.e., a sampler, having a straight profile longitudinal direction course 16 and a linear opening longitudinal direction course 20, is provided in the housing chamber 8 enclosed by the housing 2. The sampler includes a slitted hollow body 39 in which a hollow cylindrical sampling region 19 (see FIG. 9a) for collecting sample material extends along the straight profile longitudinal direction course 16. The entry opening 21 of the sampling region at the periphery thereof has a width (see FIG. 9a) which is considerably smaller than the diameter of the sampling region 19 that has a circular cross-section. The width of the withdrawal element 13 in its movement direction is considerably smaller than the diameter D. As shown in FIG. 12, for example, the entry opening 21 extends in a longitudinal portion which in a projection view extends from the lowermost to the topmost apex of the opening cross-section 32 in a superposed position or overlap with the circular opening cross-section 32. Thus, the length of the entry opening 21 corresponds to the diameter D of the opening cross-section 32. The sampling region 19 is closed at the upper lengthwise end. At its lower lengthwise end, the sampling region 19 has an exit opening 27 on the end-face side, through which sample material that has passed into the hollow body 39, passes, via an open space 40 in the lower wall projection 36, into a funnel 41, from the tapered end 42 of which the sample material may be removed from the device 1.

The so-called opening longitudinal direction course 20 of the entry opening 21 shown in FIG. 9b also corresponds to a straight line. To allow a defined translational movement pattern of the withdrawal element 13 in the housing chamber 8, in the example, the hollow body 39 of the sampler at both its lengthwise ends merges in one piece into a frame 43 whose cross-section fills the recess 34 so as to form a longitudinal guide. The displacement direction 45 corresponds to the longitudinal direction of the recess 34, i.e., extends perpendicularly with respect to the longitudinal direction of the entry opening 21. The displacement direction as well as the longitudinal direction of the entry opening extend perpendicularly with respect to the longitudinal center line x-x, i.e., perpendicularly with respect to the flow direction 7 in the line portions 5. By way of the hollow body 39, the frame 43 bounds two frame openings 44, which accommodate the diameter D of the opening cross-sections 32. The displacement path is dimensioned to be large enough that, according to the projection view in FIGS. 11 to 14, the opening cross-section 32 facing the entry opening 21 may be completely traversed by the entry opening 21. In addition, there is the option, shown in FIGS. 11 and 14, to completely move the hollow body 39 or the entire withdrawal element 13 out of an overlap with the opening cross-section 32. In these edge positions (see FIGS. 11, 14), the frame 43 also does not overlap with the opening cross-sections 32, so that an undisturbed flow is made possible. FIGS. 11a to 14a show an observation plane 30 which extends perpendicularly with respect to the plane of the drawing, leads centrally through the hollow body 39 and extends transversely with respect to the displacement direction 45 of the frame 43. The observation plane 30 is thus moved together with the withdrawal element 13. At the same time, this line, illustrated by dashed lines in the figures, corresponds to the course of an intersection line 33 between the observation plane 30 and a reference plane 31, situated in the plane of the drawing, which extends perpendicularly with respect to the observation plane 30 and to the opening cross-sections 32. As a result of the described guide means, the orientation of the hollow body 39, and thus of the withdrawal element 13, remains unchanged with respect to the intersection line 33 during the movement in the observation plane 30. In other words, in the example this means that the straight opening longitudinal direction course 20 in the observation plane 30 always extends perpendicular to the reference plane 31 and to the intersection line 33. The withdrawal element 13 and its hollow body 39 used for collecting sample material may be moved, for example, by manually displacing the frame 43, or alternatively, a linear drive engaging with the frame 43 could be used.

In both exemplary embodiments, the device according to the invention has been installed in a horizontally extending line. However, it is understood that this illustration is only by way of example, and that, if necessary, the device according to the invention could also be installed in a line having any desired different course.

All features disclosed are (in themselves) pertinent to the invention. The disclosure content of the associated/accompanying priority documents (copy of the prior application) is also hereby included in full in the disclosure of the application, including for the purpose of incorporating features of these documents in claims of the present application. The subsidiary claims in their optional subordinated formulation characterize independent inventive refinement of the prior art, in particular to undertake divisional applications based on these claims.

The invention claimed is:

1. A device for withdrawing samples from free-flowing and/or liquid and/or gaseous material
   comprising a housing having a housing chamber which has two connection openings, spaced apart from one another, for connecting in each case a line portion through which a material flow may flow, the two connection openings in particular having identical opening cross-sections;
   a withdrawal element which is movable in the housing chamber,
   the withdrawal element being formed in the shape of a cross-section extruded along a profile longitudinal direction course
   the withdrawal element bounding a hollow sampling region which extends along the profile longitudinal direction course and is in fluid communication with the housing chamber via an entry opening in the form of a groove or slit in the withdrawal element which extends along an opening longitudinal course; and
   guide means configured to guide the withdrawal element along a defined movement pattern, via which, at least one of the two opening cross-sections is traversed by the hollow sampling region,
   wherein the profile longitudinal direction course extends, with constant azimuthal angle, along a geometric spherical surface and the defined movement pattern of the withdrawal element is along said geometric spherical surface and carried out by rotation of the withdrawal element about a rotational axis.

2. The device according to claim 1, further comprising:
   two line portions, each being connected to one of the two connection openings, wherein at least one line portion extends horizontally or substantially horizontally from its respective connection opening.

3. The device of claim 2, wherein the housing chamber has an inner wall portion between the two connection openings which extends parallel to the geometric spherical surface and conforms without play to a back surface of the withdrawal element during a portion of its movement.

4. The device of claim 2, wherein the withdrawal element may be completely moved, in a projection view in each case perpendicular to the opening cross-sections, out of an overlap with one opening cross-section or with both opening cross-sections.

5. The device of claim 4, wherein the withdrawal element, at two possible positions within its movement path which are opposite one another, may be completely moved, in a projection view in each case perpendicular to the opening cross-sections, out of an overlap with one opening cross-section or with both opening cross-sections 5.

6. The device of claim 2, wherein at at least one lengthwise end, the hollow sampling region merges into an exit opening which is enclosed along its entire periphery.

7. The device of claim 2, wherein the length of the entry opening in the opening longitudinal direction course is equal to or greater than a diameter of one of the opening cross-sections.

8. The device of claim 2, wherein the width (b) of the entry opening transverse to the opening longitudinal direction course and/or the width of the cross-section of the hollow sampling region transverse to the profile longitudinal direction course is/are continuous, and is/are smaller than the diameter of one of the opening cross-sections.

9. The device of claim 2, wherein the opening cross-sections of the two connection openings are situated parallel to one another at a distance from one another, and situated concentrically with respect to one another in a projection direction perpendicular to their cross-sectional planes.

10. The device of claim 2, wherein the movement direction of the withdrawal element is oriented transversely, with respect to the opening longitudinal direction course of the withdrawal element.

11. The device of claim 2, wherein a drive device is provided for movement of the withdrawal element, the drive device being adapted to a movement of the withdrawal element at a constant speed or at a speed that varies with time.

12. The device of claim 2, wherein there is no rotational stop, so that the withdrawal element may rotate about the rotational axis without limitation.

13. A method for withdrawing samples from free-flowing and/or liquid and/or gaseous material, comprising:
  providing a device for sampling, the device comprising: a housing having a housing chamber which has two connection openings, spaced apart from one another, for connecting in each case a line portion through which a material flow may flow, the two connection openings in particular having identical opening cross-sections; a withdrawal element which is movable in the housing chamber, the withdrawal element being formed in the shape of a cross-section extruded along a profile longitudinal direction course, the withdrawal element bounding a hollow sampling region which extends along the profile longitudinal direction course and is in fluid communication with the housing chamber via an entry opening in the form of a groove or slit in the withdrawal element which extends along an opening longitudinal course; and guide means configured to guide the withdrawal element along a defined movement pattern, via which, at least one of the two opening cross-sections is traversed by the hollow sampling region, wherein the profile longitudinal direction course extends, with constant azimuthal angle, along a geometric spherical surface and the defined movement pattern of the withdrawal element is along said geometric spherical surface and carried out by rotation of the withdrawal element about a rotational axis;
  conducting a material flow through the housing by means of the two connection openings; and
  moving the withdrawal element according to the defined movement pattern.

14. The method of claim 13, wherein, during the step of moving the withdrawal element, a back surface of the withdrawal element conforms to, with no play, and moves with, an inner wall portion of the housing located between the two connection openings, said inner wall portion extending parallel to the geometric spherical surface.

15. The method according to claim 13, further comprising:
  performing a collection operation, wherein the withdrawal element traverses, at least once, a portion of the geometric spherical surface corresponding to a transverse projection of at least one of the opening cross-sections while the material flow flows through the housing,
  wherein, during the collection operation, a sample of the material flow is collected through the entry opening and into the hollow sampling region of the withdrawal element.

* * * * *